(12) United States Patent
Ostroff et al.

(10) Patent No.: US 7,194,309 B2
(45) Date of Patent: Mar. 20, 2007

(54) PACKAGING TECHNOLOGY FOR NON-TRANSVENOUS CARDIOVERTER/DEFIBRILLATOR DEVICES

(75) Inventors: Alan H. Ostroff, San Clemente, CA (US); William J. Rissmann, Coto de Caza, CA (US); Gust H. Bardy, Seattle, WA (US)

(73) Assignee: Cameron Health, Inc., San Clemente, CA (US)

( * ) Notice: Subject to any disclaimer, the term of this patent is extended or adjusted under 35 U.S.C. 154(b) by 773 days.

(21) Appl. No.: 10/011,607

(22) Filed: Nov. 5, 2001

(65) Prior Publication Data

US 2002/0107546 A1 Aug. 8, 2002

Related U.S. Application Data

(63) Continuation-in-part of application No. 09/663,607, filed on Sep. 18, 2000, now Pat. No. 6,721,597, and a continuation-in-part of application No. 09/663,606, filed on Sep. 18, 2000, now Pat. No. 6,647,292.

(51) Int. Cl.
*A61N 1/375* (2006.01)
*A61N 1/39* (2006.01)

(52) U.S. Cl. ............................. 607/36; 607/5
(58) Field of Classification Search ............... 607/1–2, 607/4–5, 36–37
See application file for complete search history.

(56) References Cited

U.S. PATENT DOCUMENTS

| | | | |
|---|---|---|---|
| 3,653,387 A | 4/1972 | Ceier | |
| 3,710,374 A | 1/1973 | Kelly | |
| 3,911,925 A | 10/1975 | Tillery, Jr. | |
| 4,127,134 A * | 11/1978 | Ushakoff | 607/9 |
| 4,157,720 A | 6/1979 | Greatbatch | |
| 4,191,942 A | 3/1980 | Long | |
| 4,223,678 A | 9/1980 | Langer et al. | |
| 4,248,237 A | 2/1981 | Kenny | |
| 4,291,707 A | 9/1981 | Heilman et al. | |
| 4,314,095 A | 2/1982 | Moore et al. | |
| 4,402,322 A | 9/1983 | Duggan | |
| 4,407,288 A | 10/1983 | Langer et al. | |
| 4,424,818 A | 1/1984 | Doring et al. | |
| 4,450,527 A | 5/1984 | Sramek | |

(Continued)

FOREIGN PATENT DOCUMENTS

DE 298 01 807 U1 7/1998

(Continued)

OTHER PUBLICATIONS

U.S. Appl. No. 09/663,607 to Bardy et al., filed Sep. 18, 2000.

(Continued)

*Primary Examiner*—Kristen Mullen
(74) *Attorney, Agent, or Firm*—Crompton, Seager & Tufte, LLC

(57) ABSTRACT

Packaging techniques for a non-transvenous implantable cardioverter/defibrillator include a housing and a frame within the housing for holding electronic components. A header is disposed on the housing and includes at least one feedthrough extending through the housing for providing electrical communication to and from the electronic components within the housing.

78 Claims, 11 Drawing Sheets

U.S. PATENT DOCUMENTS

| | | | |
|---|---|---|---|
| 4,567,900 A | 2/1986 | Moore | |
| 4,602,637 A | 7/1986 | Elmqvist et al. | |
| 4,603,705 A | 8/1986 | Speicher et al. | |
| 4,693,253 A | 9/1987 | Adams | |
| 4,765,341 A | 8/1988 | Mower et al. | |
| 4,800,883 A | 1/1989 | Winstrom | |
| 4,830,005 A | 5/1989 | Woskow | |
| 4,944,300 A | 7/1990 | Saksena | |
| 5,105,810 A | 4/1992 | Collins et al. | |
| 5,109,842 A | 5/1992 | Adinolfi | |
| 5,129,392 A | 7/1992 | Bardy et al. | |
| 5,133,353 A | 7/1992 | Hauser | |
| 5,144,946 A | 9/1992 | Weinberg et al. | |
| 5,184,616 A | 2/1993 | Weiss | |
| 5,191,901 A | 3/1993 | Dahl et al. | |
| 5,203,348 A | 4/1993 | Dahl et al. | |
| 5,230,337 A | 7/1993 | Dahl et al. | |
| 5,255,692 A | 10/1993 | Neubauer et al. | |
| 5,261,400 A | 11/1993 | Bardy | |
| 5,300,106 A | 4/1994 | Dahl et al. | |
| 5,331,966 A | 7/1994 | Bennett et al. | |
| 5,342,407 A | 8/1994 | Dahl et al. | |
| 5,344,432 A * | 9/1994 | Slettenmark et al. | 607/36 |
| 5,366,496 A | 11/1994 | Dahl et al. | |
| 5,370,669 A * | 12/1994 | Daglow et al. | 607/36 |
| 5,376,103 A | 12/1994 | Anderson et al. | |
| 5,376,104 A | 12/1994 | Sakai et al. | |
| 5,385,574 A * | 1/1995 | Hauser et al. | 607/4 |
| 5,391,200 A | 2/1995 | KenKnight et al. | |
| 5,405,363 A | 4/1995 | Kroll et al. | |
| 5,411,539 A | 5/1995 | Neisz | |
| 5,411,547 A | 5/1995 | Causey, III | |
| 5,413,591 A | 5/1995 | Knoll | |
| 5,423,326 A | 6/1995 | Wang et al. | |
| 5,476,503 A | 12/1995 | Yang | |
| 5,509,923 A | 4/1996 | Middleman et al. | |
| 5,509,928 A | 4/1996 | Acken | |
| 5,531,765 A | 7/1996 | Pless | |
| 5,531,766 A | 7/1996 | Kroll et al. | |
| 5,534,019 A | 7/1996 | Paspa | |
| 5,534,022 A | 7/1996 | Hoffmann et al. | |
| 5,545,188 A * | 8/1996 | Bradshaw et al. | 607/37 |
| 5,597,956 A | 1/1997 | Ito et al. | |
| 5,601,607 A * | 2/1997 | Adams | 607/5 |
| 5,603,732 A | 2/1997 | Dahl et al. | |
| 5,618,287 A | 4/1997 | Fogarty et al. | |
| 5,620,477 A | 4/1997 | Pless et al. | |
| 5,643,328 A | 7/1997 | Cooke et al. | |
| 5,645,586 A | 7/1997 | Meltzer | |
| 5,658,317 A | 8/1997 | Haefner et al. | |
| 5,658,321 A | 8/1997 | Fayram et al. | |
| 5,674,260 A | 10/1997 | Weinberg | |
| 5,690,648 A | 11/1997 | Fogarty et al. | |
| 5,690,683 A | 11/1997 | Haefner et al. | |
| 5,697,953 A | 12/1997 | Kroll et al. | |
| 5,713,926 A | 2/1998 | Hauser et al. | |
| 5,766,226 A | 6/1998 | Pedersen | |
| 5,776,169 A | 7/1998 | Schroeppel | |
| 5,814,090 A | 9/1998 | Latterell et al. | |
| 5,836,976 A | 11/1998 | Min et al. | |
| 5,895,414 A | 4/1999 | Sanchez-Zambrano | |
| 5,919,211 A | 7/1999 | Adams | |
| 5,919,222 A | 7/1999 | Hjelle et al. | |
| 5,925,069 A | 7/1999 | Graves et al. | |
| 5,935,154 A | 8/1999 | Westlund | |
| 5,941,904 A | 8/1999 | Johnston et al. | |
| 5,963,429 A * | 10/1999 | Chen | 361/764 |
| 6,014,586 A | 1/2000 | Weinberg et al. | |
| 6,026,325 A | 2/2000 | Weinberg et al. | |
| 6,058,328 A | 5/2000 | Levine et al. | |
| 6,093,173 A | 7/2000 | Balceta et al. | |
| 6,095,987 A | 8/2000 | Shmulewitz et al. | |
| H1905 H | 10/2000 | Hill | |
| 6,128,531 A | 10/2000 | Campbell-Smith | |
| 6,144,866 A | 11/2000 | Miesel et al. | |
| 6,185,450 B1 | 2/2001 | Seguine et al. | |
| 6,411,844 B1 | 6/2002 | Kroll et al. | |
| 6,647,292 B1 | 11/2003 | Bardy et al. | |
| 6,658,296 B1 * | 12/2003 | Wong et al. | 607/37 |
| 2001/0027330 A1 | 10/2001 | Sullivan et al. | |
| 2002/0068958 A1 | 6/2002 | Bardy et al. | |

FOREIGN PATENT DOCUMENTS

| | | |
|---|---|---|
| EP | 0 095 727 A1 | 12/1983 |
| EP | 0 316 616 A2 | 5/1989 |
| EP | 0 316 616 A3 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | 1 000 634 A1 | 5/2000 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | WO 02/068046 A1 | 9/2002 |
| WO | WO 03/018121 A2 | 3/2003 |

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Mirowski, M. et al., "Automatic Detection and Defibrillation of Lethal Arrhythmias-A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defribrillator," *IEEE*, (1987) pp. 167-170.

Schuder, John C., "Completely Implanted Defibrillator," *JAMA*, vol. 214, No. 6, Nov. 9, 1970. p. 1123 (single sheet).

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Tietze U. et al., "Halbleiter-Schaltungstechnik," © Springer-Verlag (Berlin, Germany), (1991), pp. 784-786.

Walters, R.A. et al., "Analog to Digital Conversion Techniques in Implantable Devices," *Annual International Conference of the IEEE Engineering in Medicine and Biology Society*, vol. 13 No. 4 (1991) p. 1674-1676.

\* cited by examiner

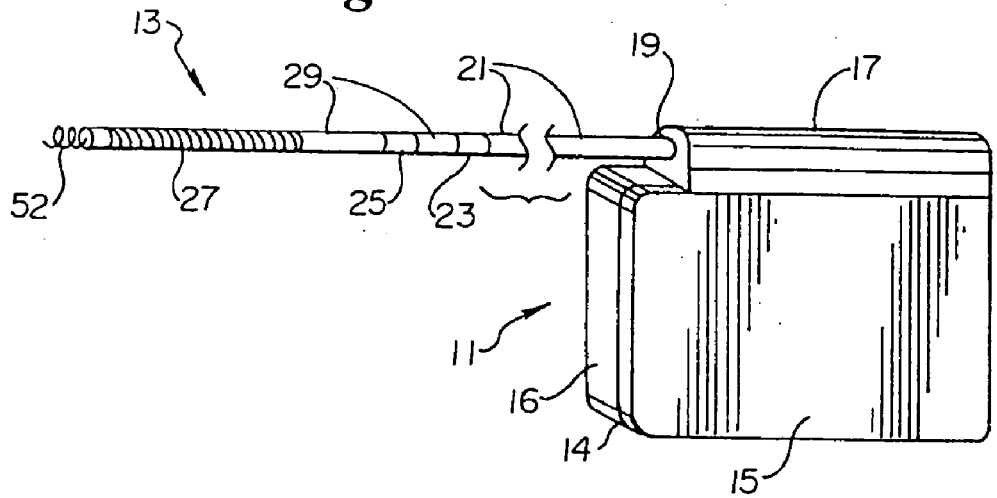
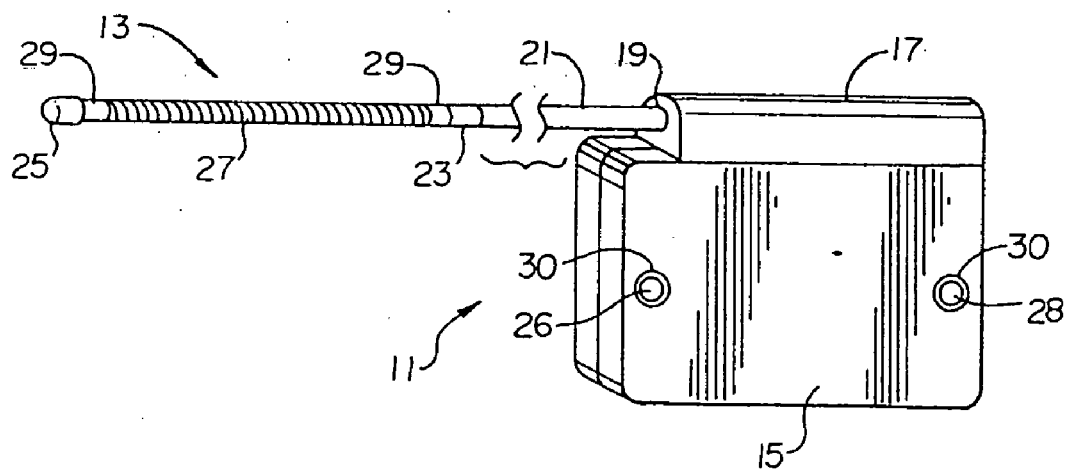
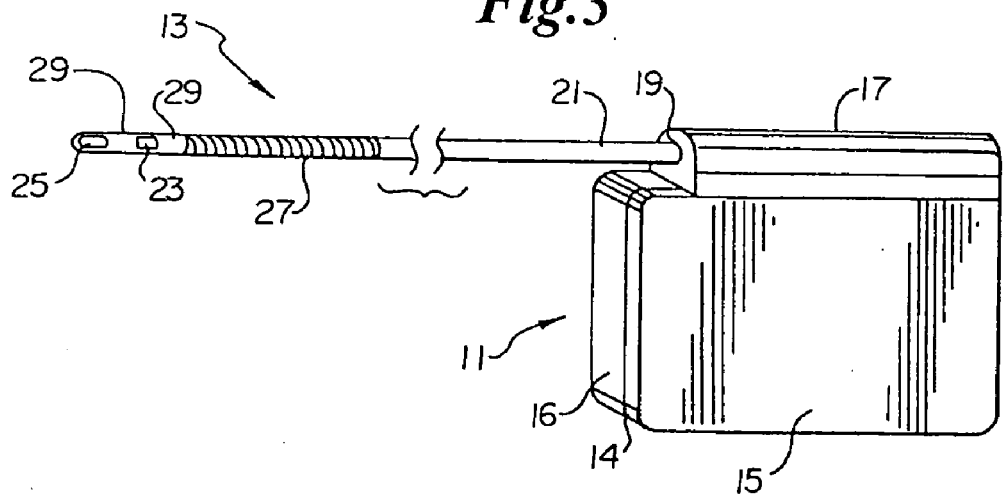

PACKAGING TECHNOLOGY FOR NON-TRANSVENOUS CARDIOVERTER/DEFIBRILLATOR DEVICES

CROSS REFERENCE TO RELATED APPLICATIONS

The present application is a continuation in part of U.S. patent application entitled "SUBCUTANEOUS ONLY IMPLANTABLE CARDIOVERTER-DEFIBRILLATOR AND OPTIONAL PACER," having Ser. No. 09/663,607, filed Sep. 18, 2000, now U.S. Pat. No. 6,721,597 and U.S. patent application entitled "UNITARY SUBCUTANEOUS ONLY IMPLANTABLE CARDIOVERTER-DEFIBRILLATOR AND OPTIONAL PACER," having Ser. No. 09/663,606, filed Sep. 18, 2000, now U.S. Pat. No. 6,647,292 of which both applications are assigned to the assignee of the present application, and the disclosures of both applications are hereby incorporated by reference.

Applications related to the foregoing applications include a U.S. patent application entitled "DUCKBILL-SHAPED IMPLANTABLE CARDIOVERTER-DEFIBRILLATOR AND METHOD OF USE," U.S. patent application entitled "CERAMICS AND/OR OTHER MATERIAL INSULATED SHELL FOR ACTIVE AND NON-ACTIVE S-ICD CAN," U.S. patent application entitled "SUBCUTANEOUS ELECTRODE FOR TRANSTHORACIC CONDUCTION WITH IMPROVED INSTALLATION CHARACTERISTICS," U.S. patent application entitled "SUBCUTANEOUS ELECTRODE WITH IMPROVED CONTACT SHAPE FOR TRANSTHORACIC CONDUCTION," U.S. patent application entitled "SUBCUTANEOUS ELECTRODE FOR TRANSTHORACIC CONDUCTION WITH HIGHLY MANEUVERABLE INSERTION TOOL," U.S. patent application entitled "SUBCUTANEOUS ELECTRODE FOR TRANSTHORACIC CONDUCTION WITH LOW-PROFILE INSTALLATION APPENDAGE AND METHOD OF DOING SAME," U.S. patent application entitled "SUBCUTANEOUS ELECTRODE FOR TRANSTHORACIC CONDUCTION WITH INSERTION TOOL," U.S. patent application entitled "METHOD OF INSERTION AND IMPLANTATION FOR IMPLANTABLE CARDIOVERTER-DEFIBRILLATOR CANISTERS," U.S. patent application entitled "CANISTER DESIGNS FOR IMPLANTABLE CARDIOVERTER-DEFIBRILLATORS," U.S. patent application entitled "RADIAN CURVED IMPLANTABLE CARDIOVERTER-DEFIBRILLATOR CANISTER," U.S. patent application entitled "CARDIOVERTER-DEFIBRILLATOR HAVING A FOCUSED SHOCKING AREA AND ORIENTATION THEREOF," U.S. patent application entitled "BIPHASIC WAVEFORM FOR ANTI-BRADYCARDIA PACING FOR A SUBCUTANEOUS IMPLANTABLE CARDIOVERTER-DEFIBRILLATOR," and U.S. patent application entitled "BIPHASIC WAVEFORM FOR ANTI-TACHYCARDIA PACING FOR A SUBCUTANEOUS IMPLANTABLE CARDIOVERTER-DEFIBRILLATOR," the disclosures of which applications are hereby incorporated by reference.

FIELD OF THE INVENTION

The subject invention relates generally to packaging and fabrication technology and finds particular application in packaging for subcutaneous implantable cardioverter/defibrillators.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters that typically enter the subclavian venous system, pass through the superior vena cava and, into one or more endocardial areas of the heart. Such electrode systems are called intravascular or transvenous electrodes. U.S. Pat. Nos. 4,603,705, 4,693,253, 4,944,300, 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353, 5,261,400, 5,620,477, and 5,658,321 the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

SUMMARY

According to one aspect of the invention, a non-transvenous implantable cardioverter/defibrillator includes a housing having a frame that holds a power storage circuit connected to a power source and an electronic package disposed on a substrate. The electronic package, the power source and the power storage device are electrically coupled to the frame. A header is fixed on a portion of the outer surface of the housing. The header includes at least one feedthrough that extends through the housing to allow electrical communication to and from the electronic package within the housing while keeping a hermetically sealed housing.

BRIEF DESCRIPTION OF THE DRAWINGS

For a better understanding of the invention, reference is now made to the drawings where like numerals represent similar objects throughout the figures where:

FIG. 1 is a schematic view of a Subcutaneous ICD (S-ICD) of the present invention;

FIG. 2 is a schematic view of an alternate embodiment of a subcutaneous electrode of the present invention;

FIG. 3 is a schematic view of an alternate embodiment of a subcutaneous electrode of the present invention;

DETAILED DESCRIPTION OF ILLUSTRATIVE EMBODIMENTS

Figure 4:
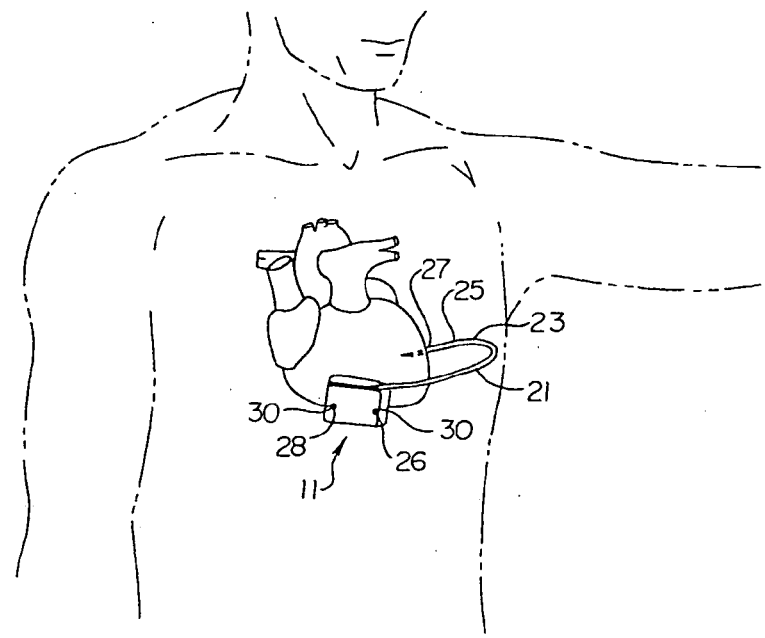
FIG. 4 is a schematic view of the S-ICD and lead of FIG. 1 subcutaneously implanted in the thorax of a patient.

Turning now to FIG. 1, the S-ICD of the present invention is illustrated. The S-ICD consists of an electrically active canister 11 and a subcutaneous electrode 13 attached to the canister. The canister has an electrically active surface 15 that is electrically insulated from the electrode connector block 17 and the canister housing 16 via insulating area 14. The canister can be similar to numerous electrically active canisters commercially available in that the canister will contain a battery supply, capacitor and operational circuitry. Alternatively, the canister can be thin and elongated to conform to the intercostal space. The circuitry will be able to monitor cardiac rhythms for tachycardia and fibrillation, and if detected, will initiate charging the capacitor and then delivering cardioversion/defibrillation energy through the active surface of the housing and to the subcutaneous electrode. Examples of such circuitry are described in U.S. Pat. Nos. 4,693,253 and 5,105,810, the entire disclosures of which are herein incorporated by reference. The canister circuitry can provide cardioversion/defibrillation energy in different types of waveforms. In one embodiment, a 100 uF biphasic waveform is used of approximately 10–20 ms total duration and with the initial phase containing approximately ⅔ of the energy, however, any type of waveform can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the active surface and the subcutaneous electrode. Pacing stimuli can be biphasic in one embodiment and similar in pulse amplitude to that used for conventional transthoracic pacing.

This same circuitry can also be used to deliver low amplitude shocks on the T-wave for induction of ventricular fibrillation for testing S-ICD performance in treating V-Fib as is described in U.S. Pat. No. 5,129,392, the entire disclosure of which is hereby incorporated by reference. Also the circuitry can be provided with rapid induction of ventricular fibrillation or ventricular tachycardia using rapid ventricular pacing. Another optional way for inducing ventricular fibrillation would be to provide a continuous low voltage, i.e., about 3 volts, across the heart during the entire cardiac cycle.

Another optional aspect of the present invention is that the operational circuitry can detect the presence of atrial fibrillation as described in Olson, W. et al. "Onset And Stability For Ventricular Tachyarrhythmia Detection in an Implantable Cardioverter and Defibrillator," Computers in Cardiology (1986) pp. 167–170. Detection can be provided via R—R Cycle length instability detection algorithms. Once atrial fibrillation has been detected, the operational circuitry will then provide QRS synchronized atrial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize in its most direct form, a rate detection algorithm that triggers charging of the capacitor once the ventricular rate exceeds some predetermined level for a fixed period of time: for example, if the ventricular rate exceeds 240 bpm on average for more than 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining QRS beat-to-beat uniformity, QRS signal frequency content, R—R interval stability data, and signal amplitude characteristics all or part of which can be used to increase or decrease both sensitivity and specificity of S-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patent is not respiring and this lack of respiration can be used to confirm the QRS findings of cardiac arrest. The same technique can be used to provide information about the respiratory rate or estimate cardiac output as described in U.S. Pat. Nos. 6,095,987, 5,423,326, 4,450,527, the entire disclosures of which are incorporated herein by reference.

The canister of the present invention can be made out of titanium alloy or other presently preferred electrically active canister designs. However, it is contemplated that a malleable canister that can conform to the curvature of the patient's chest will be preferred. In this way the patient can have a comfortable canister that conforms to the shape of the patient's rib cage. Examples of conforming canisters are provided in U.S. Pat. No. 5,645,586, the entire disclosure of which is herein incorporated by reference. Therefore, the canister can be made out of numerous materials such as medical grade plastics, metals, and alloys. In the preferred embodiment, the canister is smaller than 60 cc volume having a weight of less than 100 gms for long term wearability, especially in children. The canister and the lead of the S-ICD can also use fractal or wrinkled surfaces to increase surface area to improve defibrillation capability. Because of the primary prevention role of the therapy and the likely need to reach energies over 40 Joules, a feature of one embodiment is that the charge time for the therapy, is intentionally left relatively long to allow capacitor charging within the limitations of device size. Examples of small ICD housings are disclosed in U.S. Pat. Nos. 5,597,956 and 5,405,363, the entire disclosures of which are herein incorporated by reference.

Different subcutaneous electrodes 13 of the present invention are illustrated in FIGS. 1–3. Turning to FIG. 1, the lead 21 for the subcutaneous electrode is preferably composed of silicone or polyurethane insulation. The electrode is connected to the canister at its proximal end via connection port 19 which is located on an electrically insulated area 17 of the canister. The electrode illustrated is a composite electrode with three different electrodes attached to the lead. In the embodiment illustrated, an optional anchor segment 52 is attached at the most distal end of the subcutaneous electrode for anchoring the electrode into soft tissue such that the electrode does not dislodge after implantation.

The most distal electrode on the composite subcutaneous electrode is a coil electrode 27 that is used for delivering the high voltage cardioversion/defibrillation energy across the heart. The coil cardioversion/defibrillation electrode is about 5–10 cm in length. Proximal to the coil electrode are two sense electrodes, a first sense electrode 25 is located proximally to the coil electrode and a second sense electrode 23 is located proximally to the first sense electrode. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 29. Similar types of cardioversion/defibrillation electrodes are currently commercially available in a transvenous configuration. For example, U.S. Pat. No. 5,534,022, the entire disclosure of which is herein incorporated by reference, disclosures a composite electrode with a coil cardioversion/defibrillation electrode and sense electrodes. Modifications to this arrangement are contemplated within the scope of the invention. One such modification is illustrated in FIG. 2 where the two sensing electrodes 25 and 23 are non-circumferential sensing electrodes and one is located at the distal end, the other is located proximal thereto with the coil electrode located in between the two sensing electrodes. In this embodiment the sense electrodes are spaced about 6 to about 12 cm apart depending on the length of the coil electrode used. FIG. 3 illustrates yet a further embodiment where the two sensing electrodes are located at the distal end to the composite electrode with the coil electrode located proximally thereto. Other possibilities exist and are contemplated within the present invention. For example, having only one sensing electrode, either proximal or distal to the coil cardioversion/defibrillation electrode with the coil serving as both a sensing electrode and a cardioversion/defibrillation electrode.

It is also contemplated within the scope of the invention that the sensing of QRS waves (and transthoracic impedance) can be carried out via sense electrodes on the canister housing or in combination with the cardioversion/defibrillation coil electrode and/or the subcutaneous lead sensing electrode(s). In this way, sensing could be performed via the one coil electrode located on the subcutaneous electrode and the active surface on the canister housing. Another possibility would be to have only one sense electrode located on the subcutaneous electrode and the sensing would be performed by that one electrode and either the coil electrode on the subcutaneous electrode or by the active surface of the canister. The use of sensing electrodes on the canister would eliminate the need for sensing electrodes on the subcutaneous electrode. It is also contemplated that the subcutaneous electrode would be provided with at least one sense electrode, the canister with at least one sense electrode, and if multiple sense electrodes are used on either the subcutaneous electrode and/or the canister, that the best QRS wave detection combination will be identified when the S-ICD is implanted and this combination can be selected, activating the best sensing arrangement from all the existing sensing possibilities. Turning again to FIG. 2, two sensing electrodes 26 and 28 are located on the electrically active surface 15 with electrical insulator rings 30 placed between the sense electrodes and the active surface. These canister sense electrodes could be switched off and electrically insulated during and shortly after defibrillation/cardioversion shock delivery. The canister sense electrodes may also be placed on the electrically inactive surface of the canister. In the embodiment of FIG. 2, there are actually four sensing electrodes, two on the subcutaneous lead and two on the canister. In the preferred embodiment, the ability to change which electrodes are used for sensing would be a programmable feature of the S-ICD to adapt to changes in the patient physiology and size (in the case of children) over time. The programming could be done via the use of physical switches on the canister, or as presently preferred, via the use of a programming wand or via a wireless connection to program the circuitry within the canister.

The canister could be employed as either a cathode or an anode of the S-ICD cardioversion/defibrillation system. If the canister is the cathode, then the subcutaneous coil electrode would be the anode. Likewise, if the canister is the anode, then the subcutaneous electrode would be the cathode.

The active canister housing will provide energy and voltage intermediate to that available with ICDs and most AEDs. The typical maximum voltage necessary for ICDs using most biphasic waveforms is approximately 750 Volts with an associated maximum energy of approximately 40 Joules. The typical maximum voltage necessary for AEDs is approximately 2000–5000 Volts with an associated maximum energy of approximately 200–360 Joules depending upon the model and waveform used. The S-ICD and the US-ICD of the present invention uses maximum voltages in the range of about 50 to about 3500 Volts and is associated with energies of about 0.5 to about 350 Joules. The capacitance of the devices can range from about 25 to about 200 micro farads.

In another embodiment, the S-ICD and US-ICD devices provide energy with a pulse width of approximately one millisecond to approximately 40 milliseconds. The devices can provide pacing current of approximately one milliamp to approximately 250 milliamps.

The sense circuitry contained within the canister is highly sensitive and specific for the presence or absence of life threatening ventricular arrhythmias. Features of the detection algorithm are programmable and the algorithm is focused on the detection of V-FIB and high rate V-TACH (>240 bpm). Although the S-ICD of the present invention may rarely be used for an actual life-threatening event, the simplicity of design and implementation allows it to be employed in large populations of patients at modest risk with modest cost by non-cardiac electrophysiologists. Consequently, the S-ICD of the present invention focuses mostly on the detection and therapy of the most malignant rhythm disorders. As part of the detection algorithm's applicability to children, the upper rate range is programmable upward for use in children, known to have rapid supraventricular tachycardias and more rapid ventricular fibrillation. Energy levels also are programmable downward in order to allow treatment of neonates and infants.

Turning now to FIG. 4, the optimal subcutaneous placement of the S-ICD of the present invention is illustrated. As would be evidence to a person skilled in the art, the actual location of the S-ICD is in a subcutaneous space that is developed during the implantation process. The heart is not exposed during this process and the heart is schematically illustrated in the figures only for help in understanding where the canister and coil electrode are three dimensionally located in the left mid-clavicular line approximately at the level of the inframammary crease at approximately the 5th rib. The lead 21 of the subcutaneous electrode traverses in a subcutaneous path around the thorax terminating with its distal electrode end at the posterior axillary line ideally just lateral to the left scapula. This way the canister and subcutaneous cardioversion/defibrillation electrode provide a reasonably good pathway for current delivery to the majority of the ventricular myocardium.

Figure 5:
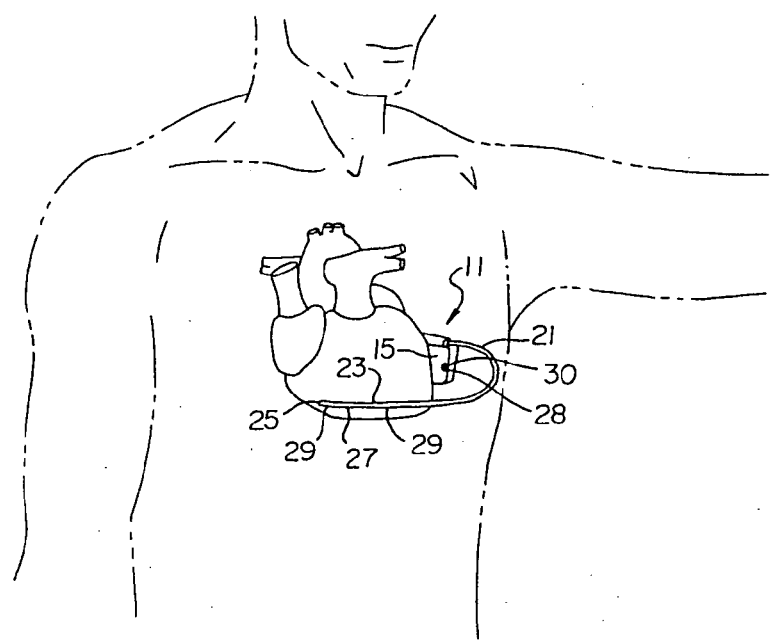
FIG. 5 is a schematic view of the S-ICD and lead of FIG. 2 subcutaneously implanted in an alternate location within the thorax of a patient.
Figure 6:
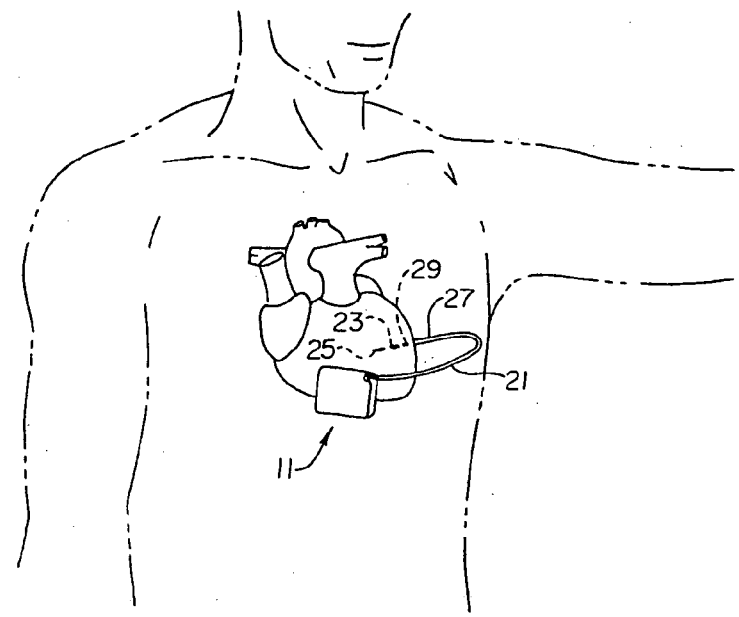
FIG. 6 is a schematic view of the S-ICD and lead of FIG. 3 subcutaneously implanted in the thorax of a patient.

FIG. 5 illustrates a different placement of the present invention. The S-ICD canister with the active housing is located in the left posterior axillary line approximately lateral to the tip of the inferior portion of the scapula. This location is especially useful in children. The lead 21 of the subcutaneous electrode traverses in a subcutaneous path around the thorax terminating with its distal electrode end at the anterior precordial region, ideally in the inframammary crease. FIG. 6 illustrates the embodiment of FIG. 1 subcutaneously implanted in the thorax with the proximal sense electrodes 23 and 25 located at approximately the left axillary line with the cardioversion/defibrillation electrode just lateral to the tip of the inferior portion of the scapula.

Figure 7:
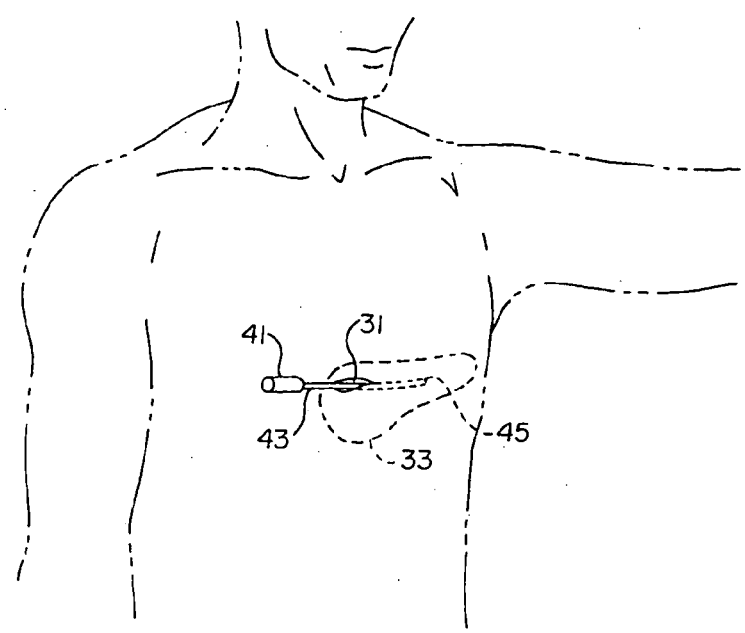
FIG. 7 is a schematic view of the method of making a subcutaneous path from the preferred incision and housing implantation point to a termination point for locating a subcutaneous electrode of the present invention.

FIG. 7 schematically illustrates the method for implanting the S-ICD of the present invention. An incision 31 is made in the left anterior axillary line approximately at the level of the cardiac apex. This incision location is distinct from that chosen for S-ICD placement and is selected specifically to allow both canister location more medially in the left inframammary crease and lead positioning more posteriorly via the introducer set (described below) around to the left posterior axillary line lateral to the left scapula. That said, the incision can be anywhere on the thorax deemed reasonably by the implanting physician although in the preferred embodiment, the S-ICD of the present invention will be applied in this region. A subcutaneous pathway 33 is then created medially to the inframmary crease for the canister and posteriorly to the left posterior axillary line lateral to the left scapula for the lead.

Figure 8:
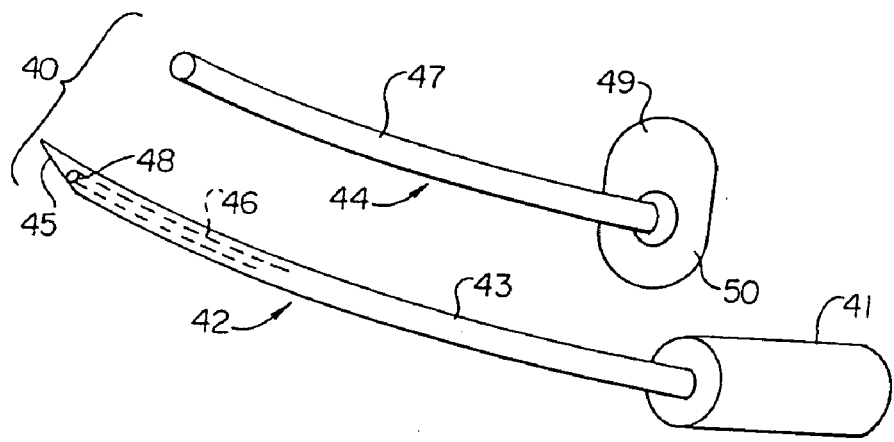
FIG. 8 is a schematic view of an introducer set for performing the method of lead insertion of any of the described embodiments.

The S-ICD canister 11 is then placed subcutaneously at the location of the incision or medially at the subcutaneous region at the left crease. The subcutaneous electrode 13 is placed with a specially designed curved introducer set 40 (see FIG. 8). The introducer set comprises a curved trocar 42 and a stiff curved peel away sheath 44. The peel away sheath is curved to allow for placement around the rib cage of the patient in the subcutaneous space created by the trocar. The sheath has to be stiff enough to allow for the placement of the electrodes without the sheath collapsing or bending. Preferably the sheath is made out of a biocompatible plastic material and is perforated along its axial length to allow for it to split apart into two sections. The trocar has a proximal handle 41 and a curved shaft 43. The distal end 45 of the trocar is tapered to allow for dissection of a subcutaneous pat 33 in the patient. Preferably, the trocar is cannulated having a central Lumen 46 and terminating in an opening 48 at the distal end. Local anesthetic such as lidocaine can be delivered, if necessary, through the lumen or through a curved and elongated needle designed to anesthetize the path to be used for trocar insertion should general anesthesia not be employed. The curved peel away sheath 44 has a proximal pull tab 49 for breaking the sheath into two halves along its axial shalt 47. The sheath is placed over a guidewire inserted through the trocar after the subcutaneous path has been created. The subcutaneous pathway is then developed until it terminates subcutaneously at a location that, if a straight line were drawn from the canister location to the path termination point the line would intersect a substantial portion of the left ventricular mass of the patient. The guidewire is then removed leaving the peel away sheath. The subcutaneous lead system is then inserted through the sheath until it is in the proper location. Once the subcutaneous lead system is in the proper location, the sheath is split in half using the pull tab 49 and removed. If more than one subcutaneous electrode is being used, a new curved peel away sheath can be used for each subcutaneous electrode.

Figure 9:
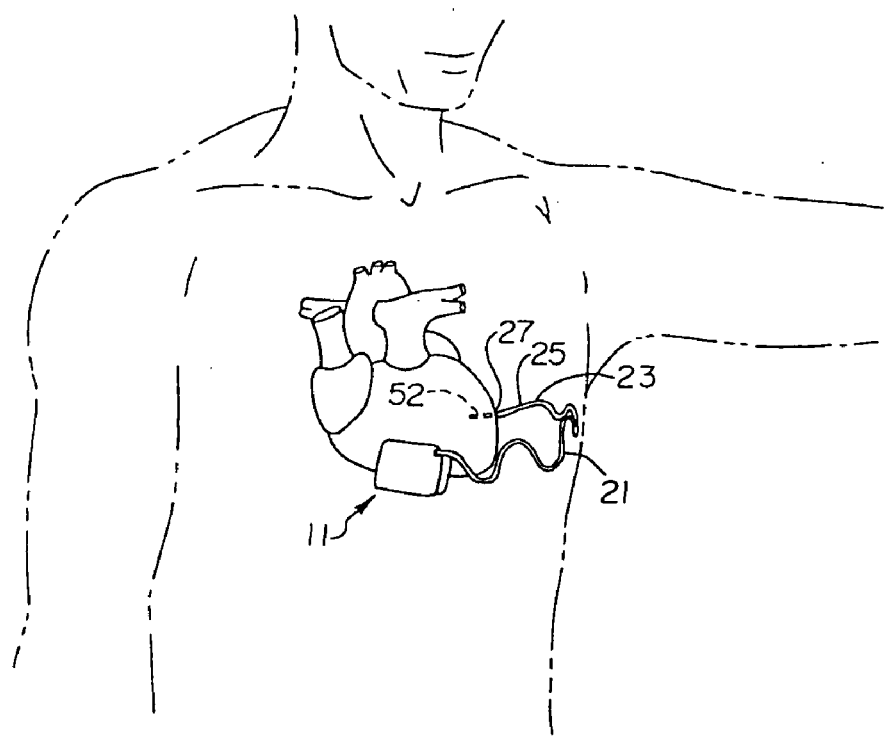
FIG. 9 is a schematic view of an alternative S-ICD of the present invention illustrating a lead subcutaneously and serpiginously implanted in the thorax of a patient for use particularly in children.

The S-ICD will have prophylactic use in adults where chronic transvenous/epicardial 10) lead systems pose excessive risk or have already resulted in difficulty, such as sepsis or lead fractures. It is also contemplated that a major use of the S-ICD system of the present invention will be for prophylactic use in children who are at risk for having fatal arrhythmias, where chronic transvenous lead systems pose significant management problems. Additionally, with the use of standard transvenous ICDs in children, problems develop during patient growth in that the lead system does not accommodate the growth. FIG. 9 illustrates the placement of the S-ICD subcutaneous lead system such that he problem that growth presents to the lead system is overcome. The distal end of the subcutaneous electrode is placed in the same location as described above providing a good location for the coil cardioversion/defibrillation electrode 27 and the sensing electrodes 23 and 25. The insulated lead 21, however is no longer placed in a taut configuration. Instead, the lead is serpiginously placed with a specially designed introducer trocar and sheath such that it has numerous waves or bends. As the child grows, the waves or bends will straighten out lengthening the lead system while maintaining proper electrode placement. Although it is expected that fibrous scarring especially around the defibrillation coil will help anchor it into position to maintain its posterior position during growth, a lead system with a distal tine or screw electrode anchoring system 52 can also be incorporated into the distal tip of the lead to facilitate lead stability (see FIG. 1). Other anchoring systems can also be used such as hooks, sutures, or the like.

Figure 10:
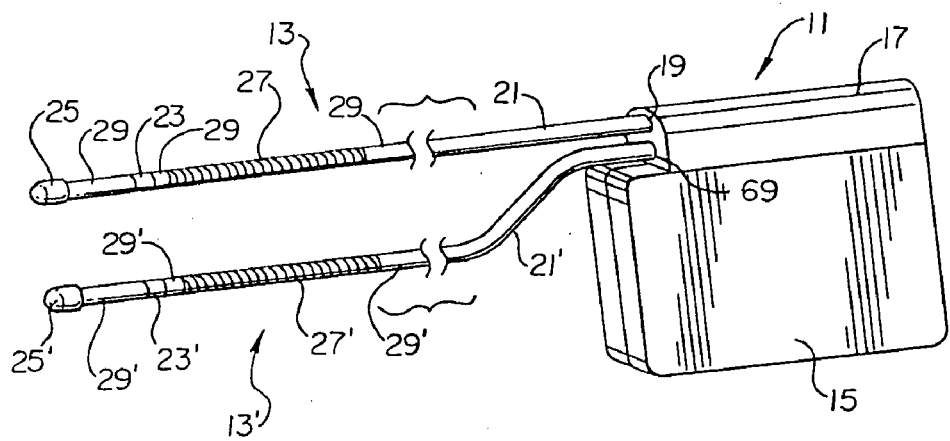
FIG. 10 is a schematic view of an alternate embodiment of an S-ICD of the present invention.
Figure 11:
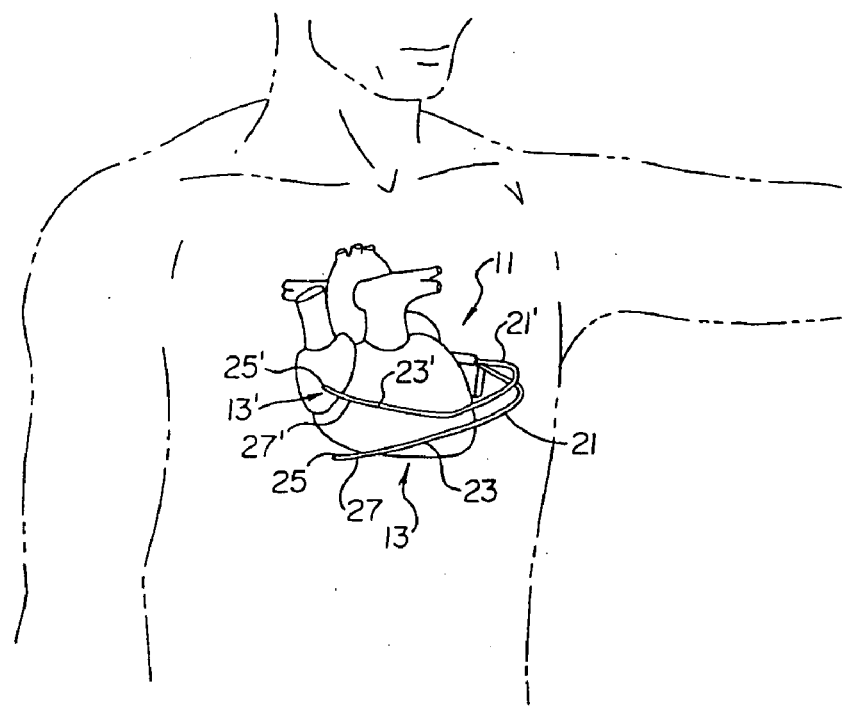
FIG. 11 is a schematic view of the S-ICD of FIG. 10 subcutaneously implanted in the thorax of a patient.

FIGS. 10 and 11 illustrate another embodiment of the present S-ICD invention. In this embodiment there are two subcutaneous electrodes 13 and 13' of opposite polarity to the canister. The additional subcutaneous electrode 13' is essentially identical to the previously described electrode. In this embodiment the cardioversion/defibrillation energy is delivered between the active surface of the canister and the two coil electrodes 27 and 27'. Additionally, provided in the canister is means for selecting the optimum sensing arrangement between the four sense electrodes 23, 23', 25, and 25'. The two electrodes are subcutaneously placed on the same side of the heart. As illustrated in FIG. 6, one subcutaneous electrode 13 is placed inferiorly and the other electrode 13' is placed superiorly. It is also contemplated with this dual subcutaneous electrode system that the canister and one subcutaneous electrode are the same polarity and the other subcutaneous electrode is the opposite polarity.

Figure 12:
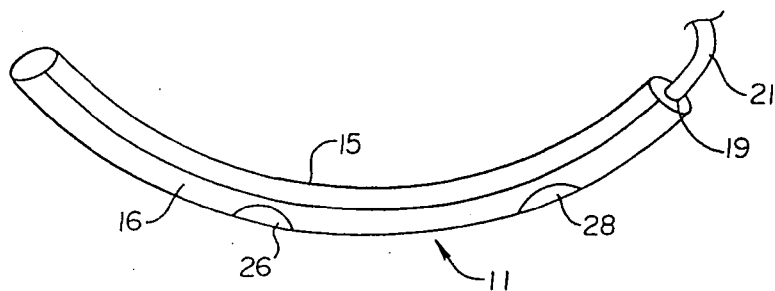
FIG. 12 is a schematic view of yet a further embodiment where the canister of the S-ICD of the present invention is shaped to be particularly useful in placing subcutaneously adjacent and parallel to a rib of a patient.
Figure 13:
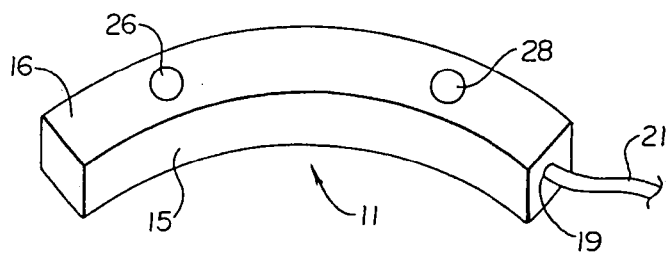
FIG. 13 is a schematic of a different embodiment where the canister of the S-ICD of the present invention is shaped to be particularly useful in placing subcutaneously adjacent and parallel to a rib of a patient.

Turning now to FIGS. 12 and 13, further embodiments are illustrated where the canister 11 of the S-ICD of the present invention is shaped to be particularly useful in placing subcutaneously adjacent and parallel to a rib of a patient. The canister is long, thin, and curved to conform to the shape of the patient's rib. In the embodiment illustrated in FIG. 12, the canister has a diameter ranging from about 0.5 cm to about 2 cm without 1 cm being presently preferred. Alternatively, instead of having a circular cross sectional area, the canister could have a rectangular or square cross sectional area as illustrated in FIG. 13 without falling outside of the scope of the present invention. The length of the canister can vary depending on the size of the patient's thorax. In an embodiment, the canister is about 5 cm to about 40 cm long. The canister is curved to conform to the curvature of the ribs of the thorax. The radius of the curvature will vary depending on the size of the patient, with smaller radiuses for smaller patients and larger radiuses for larger patients. The radius of the curvature can range from about 5 cm to about 35 cm depending on the size of the patient. Additionally, the radius of the curvature need not be uniform throughout the canister such that it can be shaped closer to the shape of the ribs. The canister has an active surface, 15 that is located on the interior (concave) portion of the curvature and an inactive surface 16 that is located on the exterior (convex) portion of the curvature. The leads of these embodiments, which are not illustrated except for the attachment port 19 and the proximal end of the lead 21, can be any of the leads previously described above, with the lead illustrated in FIG. 1 being presently preferred.

The circuitry of this canister is similar to the circuitry described above. Additionally, the canister can optionally have at least one sense electrode located on either the active surface of the inactive surface and the circuitry within the canister can be programmable as described above to allow for the selection of the best sense electrodes. It is presently preferred that the canister have two sense electrodes 26 and 28 located on the inactive surface of the canisters as illustrated, where the electrodes are spaced from about 1 to about 10 cm apart with a spacing of about 3 cm being presently preferred. However, the sense electrodes can be located on the active surface as described above.

It is envisioned that the embodiment of FIG. 12 will be subcutaneously implanted adjacent and parallel to the left anterior 5th rib, either between the 4th and 5th ribs or between the 5th and 6th ribs. However other locations can be used.

Another component of the S-ICD of the present invention is a cutaneous test electrode system designed to simulate the subcutaneous high voltage shock electrode system as well as the QRS cardiac rhythm detection system. This test electrode system is comprised of a cutaneous patch electrode of similar surface area and impedance to that of the S-ICD canister itself together with a cutaneous strip electrode comprising a defibrillation strip as well as two button electrodes for sensing of the QRS. Several cutaneous strip electrodes are available to allow for testing various bipole spacings to optimize signal detection comparable to the implantable system.

FIGS. 14 to 18 depict particular US-ICD embodiments of the present invention. The various sensing, shocking and pacing circuitry, described in detail above with respect to the S-ICD embodiments, may additionally be incorporated into the following US-ICD embodiments. Furthermore, particular aspects of any individual S-ICD embodiment discussed above may be incorporated, in whole or in part, into the US-ICD embodiments depicted in the following figures.

Figure 14:
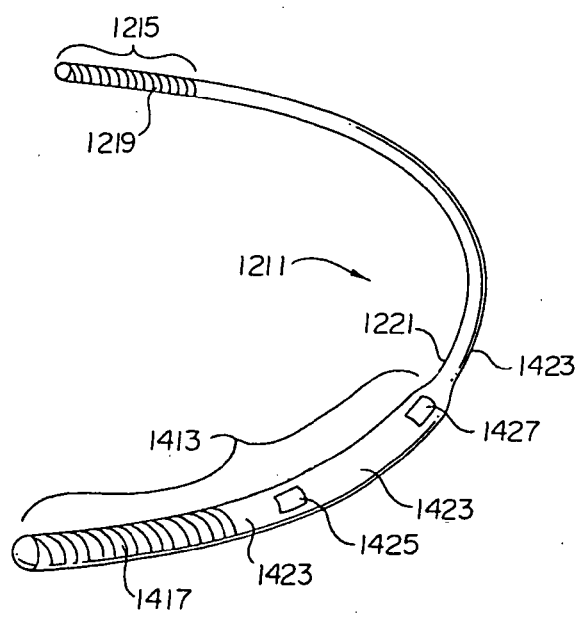
FIG. 14 is a schematic view of a Unitary Subcutaneous ICD (US-ICD) of the present invention.

Turning now to FIG. 14, the US-ICD of the present invention is illustrated. The US-ICD consists of a curved housing 1211 with a first and second end. The first end 1413 is thicker than the second end 1215. This thicker area houses a battery supply, capacitor and operational circuitry for the US-ICD. The circuitry will be able to monitor cardiac rhythms for tachycardia and fibrillation, and if detected, will initiate charging the capacitor and then delivering cardioversion/defibrillation energy through the two cardioversion/defibrillating electrodes 1417 and 1219 located on the outer surface of the two ends of the housing. The circuitry can provide cardioversion/defibrillation energy in different types of waveforms. In one embodiment, a 100 uF biphasic waveform is used of approximately 10–20 ms total duration and with the initial phase containing approximately ⅔ of the energy, however, any type of waveform can be utilized such as monophasic, biphasic, multiphasic or alternative waveforms as is known in the art.

The housing of the present invention can be made out of titanium alloy or other presently preferred ICD designs. It is contemplated that the housing is also made out of biocompatible plastic materials that electronically insulate the electrodes from each other. However, it is contemplated that a malleable canister that can conform to the curvature of the patient's chest will be preferred. In this way the patient can have a comfortable canister that conforms to the unique shape of the patient's rib cage. Examples of conforming ICD housings are provided in U.S. Pat. No. 5,645,586, the entire disclosure of which is herein incorporated by reference. In the preferred embodiment, the housing is curved in the shape of a $5^{th}$ rib of a person. Because there are many different sizes of people, the housing will come in different incremental sizes to allow a good match between the size of the rib cage and the size of the US-ICD. The length of the US-ICD will range from about 15 to about 50 cm. Because of the primary preventative role of the therapy and the need to reach energies over 40 Joules, a feature of the preferred embodiment is that the charge time for the therapy, intentionally be relatively long to allow capacitor charging within the limitations of device size.

The thick end of the housing is currently needed to allow for the placement of the battery supply, operational circuitry, and capacitors. It is contemplated that the thick end will be about 0.5 cm to about 2 cm wide with about 1 cm being presently preferred. As microtechnology advances, the thickness of the housing will become smaller.

The two cardioversion/defibrillation electrodes on the housing are used for delivering the high voltage cardioversion/defibrillation energy across the heart. In the preferred embodiment, the cardioversion/defibrillation electrodes are coil electrodes, however, other cardioversion/defibrillation electrodes could be used such as having electrically isolated active surfaces or platinum alloy electrodes. The coil cardioversion/defibrillation electrodes are about 5–10 cm in length. Located on the housing between the two cardioversion/defibrillation electrodes are two sense electrodes 1425 and 1427. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 1423. Analogous types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is to have the sense electrodes at the two ends of the housing and have the cardioversion/defibrillation electrodes located in between the sense electrodes. Another modification is to have three or more sense electrodes spaced throughout the housing and allow for the selection of the two best sensing electrodes. If three or more sensing electrodes are used, then the ability to change which electrodes are used for sensing would be a programmable feature of the US-ICD to adapt to changes in the patient physiology and size over time. The programming could be done via the use of physical switches on the canister, or as presently preferred, via the use of a programming wand or via a wireless connection to program the circuitry within the canister.

Figure 15:
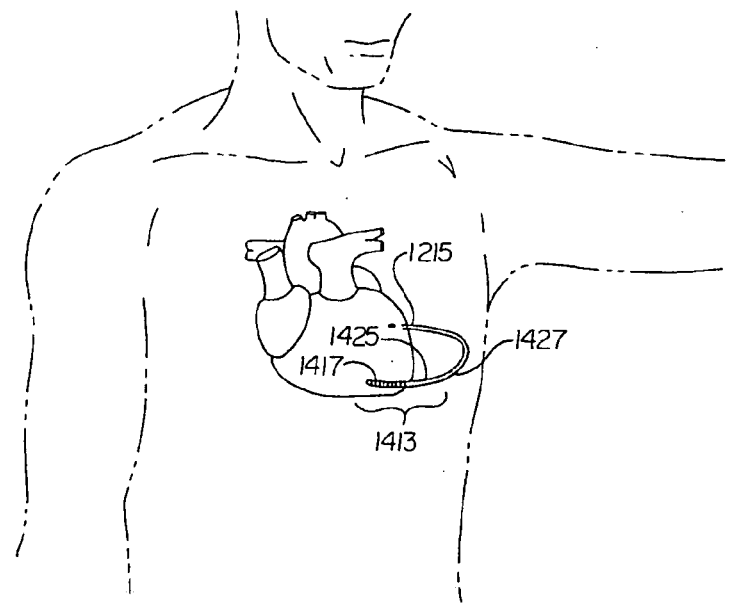
FIG. 15 is a schematic view of the US-ICD subcutaneously implanted in the thorax of a patient.

Turning now to FIG. 15, the optimal subcutaneous placement of the US-ICD of the present invention is illustrated. As would be evident to a person skilled in the art, the actual location of the US-ICD is in a subcutaneous space that is developed during the implantation process. The heart is not exposed during this process and the heart is schematically illustrated in the figures only for help in understanding where the device and its various electrodes are three dimensionally located in the thorax of the patient. The US-ICD is located between the left mid-clavicular line approximately at the level of the inframammary crease at approximately the $5^{th}$ rib and the posterior axillary line, ideally just lateral to the left scapula. This way the US-ICD provides a reasonably good pathway for current delivery to the majority of the ventricular myocardium.

Figure 16:
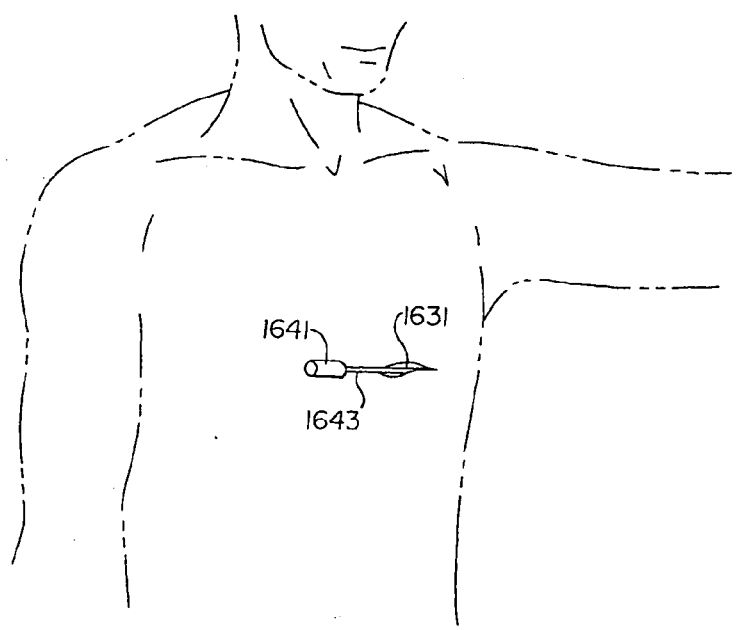
FIG. 16 is a schematic view of the method of making a subcutaneous path from the preferred incision for implanting the US-ICD.
Figure 17:
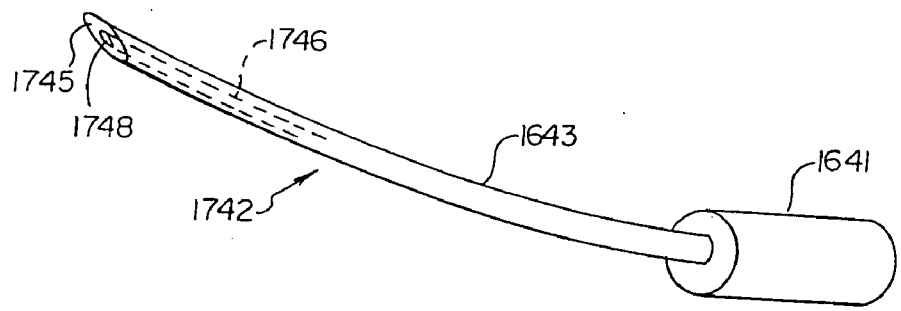
FIG. 17 is a schematic view of an introducer for performing the method of US-ICD implantation.

FIG. 16 schematically illustrates the method for implanting the US-ICD of the present invention. An incision 1631 is made in the left anterior axillary line approximately at the level of the cardiac apex. A subcutaneous pathway is then created that extends posteriorly to allow placement of the US-ICD. The incision can be anywhere on the thorax deemed reasonable by the implanting physician although in the preferred embodiment, the US-ICD of the present invention will be applied in this region. The subcutaneous pathway is created medially to the inframammary crease and extends posteriorly to the left posterior axillary line. The pathway is developed with a specially designed curved introducer 1742 (see FIG. 17). The trocar has a proximal handle 1641 and a curved shaft 1643. The distal end 1745 of the trocar is tapered to allow for dissection of a subcutaneous path in the patient. Preferably, the trocar is cannulated having a central lumen 1746 and terminating in an opening 1748 at the distal end. Local anesthetic such as lidocaine can be delivered, if necessary, through the lumen or through a curved and elongated needle designed to anesthetize the path to be used for trocar insertion should general anesthesia not be employed. Once the subcutaneous pathway is developed, the US-ICD is implanted in the subcutaneous space, the skin incision is closed using standard techniques.

Figure 18:
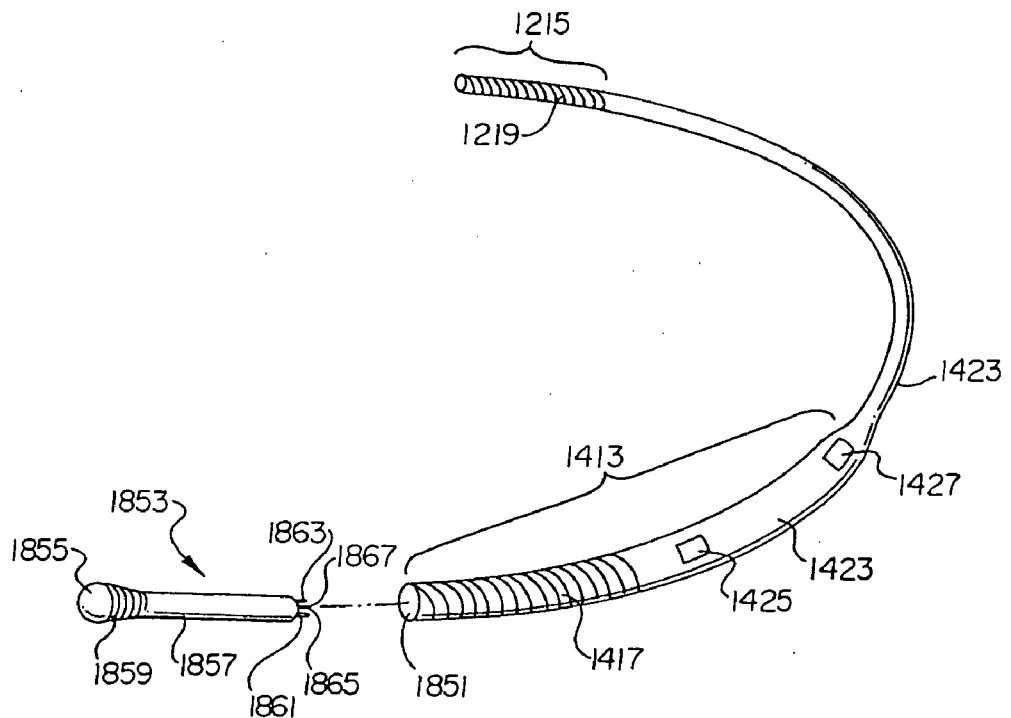
FIG. 18 is an exploded schematic view of an alternate embodiment of the present invention with a plug-in portion that contains operational circuitry and means for generating cardioversion/defibrillation shock waves.

As described previously, the US-ICDs of the present invention vary in length and curvature. The US-ICDs are provided in incremental sizes for subcutaneous implantation in different sized patients. Turning now to FIG. 18, a different embodiment is schematically illustrated in exploded view which provides different sized US-ICDs that are easier to manufacture. The different sized US-ICDs will all have the same sized and shaped thick end 1413. The thick end is hollow inside allowing for the insertion of a core operational member 1853. The core member comprises a housing 1857 which contains the battery supply, capacitor and operational circuitry for the US-ICD. The proximal end of the core member has a plurality of electronic plug connectors. Plug connectors 1861 and 1863 are electronically connected to the sense electrodes via pressure fit connectors (not illustrated) inside the thick end which are standard in the art. Plug connectors 1865 and 1867 are also electronically connected to the cardioverter/defibrillator electrodes via pressure fit connectors inside the thick end. The distal end of the core member comprises an end cap 1855, and a ribbed fitting 1859 which creates a water-tight seal when the core member is inserted into opening 1851 of the thick end of the US-ICD.

The S-ICD and US-ICD, in alternative embodiments, have the ability to detect and treat atrial rhythm disorders, including atrial fibrillation. The S-ICD and US-ICD have two or more electrodes tat provide a far-field view of cardiac electrical activity that includes the ability to record the P-wave of the electrocardiogram as well as the QRS. One can detect the onset and offset of atrial fibrillation by referencing to the P-wave recorded during normal sinus rhythm and monitoring for its change in rate, morphology, amplitude and frequency content. For example, a well-defined P-wave that abruptly disappeared and was replaced by a low-amplitude, variable morphology signal would be a strong indication of the absence of sinus rhythm and the onset of atrial fibrillation. In an alternative embodiment of a detection algorithm, the ventricular detection rate could be monitored for stability of the R—R coupling interval. In the examination of the R—R interval sequence, atrial fibrillation can be recognized by providing a near constant irregularly irregular coupling interval on a beat-by-beat basis. An R—R interval plot during AF appears "cloudlike" in appearance when several hundred or thousands of R—R intervals are plotted over time when compared to sinus rhythm or other supraventricular arrhythmias. Moreover, a distinguishing feature compared to other rhythms that are irregularly irregular, is that the QRS morphology is similar on a beat-by-beat basis despite the irregularity in the R—R coupling interval. This is a distinguishing feature of atrial fibrillation compared to ventricular fibrillation where the QRS morphology varies on a beat-by-beat basis. In yet another embodiment, atrial fibrillation may be detected by seeking to compare the timing and amplitude relationship of the detected P-wave of the electrocardiogram to the detected QRS (R-wave) of the electrocardiogram. Normal sinus rhythm has a fixed relationship that can be placed into a template matching algorithm that can be used as a reference point should the relationship change.

In other aspects of the atrial fibrillation detection process, one may include alternative electrodes that may be brought to bear in the S-ICD or US-ICD systems either by placing them in the detection algorithm circuitry through a programming maneuver or by manually adding such additional electrode systems to the S-ICD or US-ICD at the time of implant or at the time of follow-up evaluation. One may also use electrodes for the detection of atrial fibrillation that may or may not also be used for the detection of ventricular arrhythmias given the different anatomic locations of the atria and ventricles with respect to the S-ICD or US-ICD housing and surgical implant sites.

Once atrial fibrillation is detected, the arrhythmia can be treated by delivery of a synchronized shock using energy levels up to the maximum output of the device therapy for terminating atrial fibrillation or for other supraventricular arrhythmias. The S-ICD or US-ICD electrode system can be used to treat both atrial and ventricular arrhythmias not only with shock therapy but also with pacing therapy. In a further embodiment of the treatment of atrial fibrillation or other atrial arrhythmias, one may be able to use different electrode systems than what is used to treat ventricular arrhythmias. Another embodiment would be to allow for different types of therapies (amplitude, waveform, capacitance, etc.) for atrial arrhythmias compared to ventricular arrhythmias.

The core member of the different sized and shaped US-ICD will all be the same size and shape. That way, during an implantation procedure, multiple sized US-ICDs can be available for implantation, each one without a core member. Once the implantation procedure is being performed, then the correct sized US-ICD can be selected and the core member can be inserted into the US-ICD and then programmed as described above. Another advantage of this configuration is when the battery within the core member needs replacing it can be done without removing the entire US-ICD.

Figure 19:
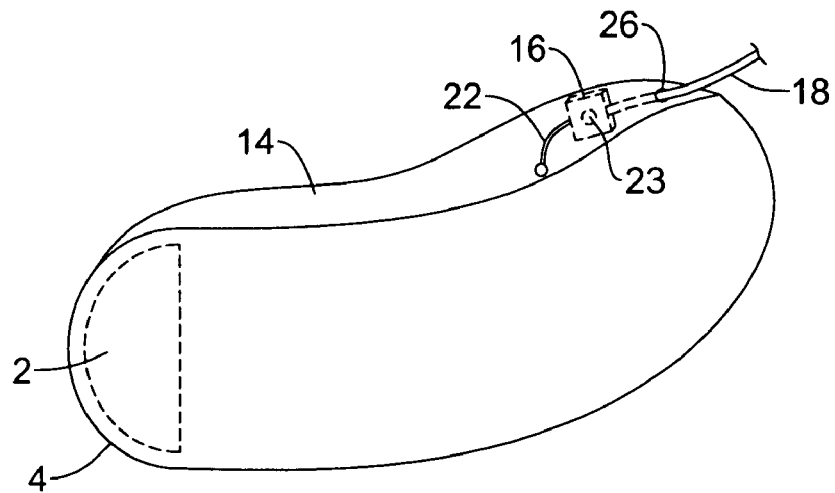
FIG. 19 illustrates an external plan view of a subcutaneous ICD according to an embodiment of the present invention.

FIG. 19 illustrates an external plan view of a subcutaneous ICD according to an embodiment of the present invention. Subcutaneous ICD 10 comprises a housing 4 that may be made of titanium, ceramic, stainless steel, Nickel alloys, or other biocompatible materials. An electrode 2 is disposed at a distal end of the housing 4. It should be noted that other embodiments of the invention may comprise different housing shapes and different numbers of electrodes disposed on the housing, as described, for example, in U.S. patent application entitled "RADIAN CURVED IMPLANTABLE CARDIOVERTER-DEFIBRILLATOR CANISTER", which is assigned to the assignee of the present invention.

According to the embodiment illustrated, the subcutaneous ICD 10 comprises a header 14 fitted along a portion of the outer surface of the housing 4. The header 14 may be pre-molded, and may comprise polyurethane, silicone, epoxy, etc. A connector block 16 is embedded in the header 14 for purposes of connecting a lead 18 and making an attachment to a feedthrough 22. The feedthrough 22 comprises a hermetic wire and may comprise plastic insulation, ceramics, glass, etc.

A hole 26 is positioned to accept the lead 18, which would normally be manually plugged in. A septum based or septum covered hole 23 is pre-slit, and is adapted to be punctured with a tool, for example, a wrench. The lead 18 is positioned in the septum hole and tightened down using a tool such as a wrench. As the lead is tightened down to a certain point, the mechanism ratches preventing overtightening and possible breakage.

Figure 20:
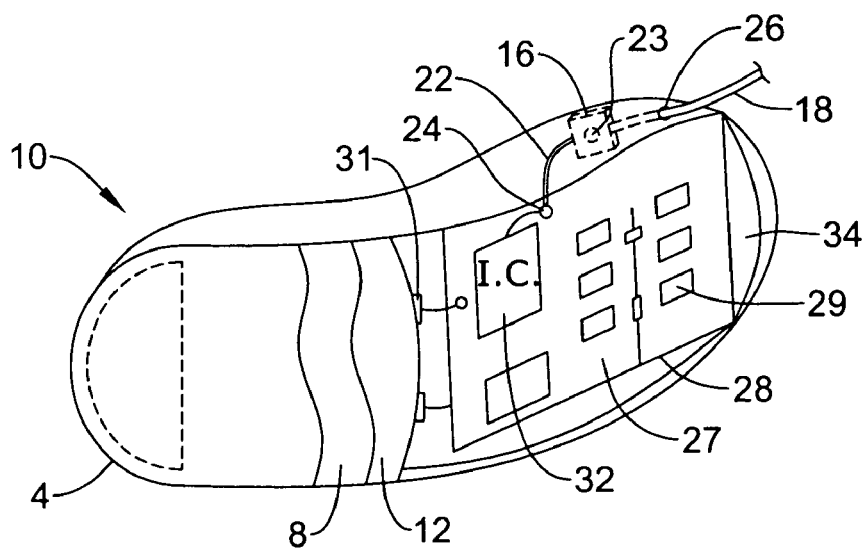
FIG. 20 illustrates a cutaway internal plan view through the housing of a subcutaneous ICD according to an embodiment of the present invention.

Referring to FIG. 20, a cutaway internal plan view through the housing of a subcutaneous ICD according to an embodiment of the present invention is illustrated. Subcutaneous ICD 10 comprises a housing 4 interrelated to a feedthrough 22 and a frame 34 that holds a power circuit 12 and an electronic package 28. An insulator 8 is positioned between the housing 4 and the circuitry inside the housing 4.

The housing 4 may be formed from two half portions adapted to fit each other to form an enclosing assembly. The housing half portions are typically welded together along their edges. Welding may be accomplished using conventional laser welding techniques as used in housing halves for implantable devices. During the welding process, the housing may be backfilled with a gas to prevent or reduce potential arching inside the housing. The gas may comprise approximately 90–95% Nitrogen gas and approximately 5–10% Helium as a marker for lead detection. In addition, a desiccant may be applied in dead spaces within the housing to absorb moisture.

The power circuit 12 includes a power source such as a battery and a power storage device such as a capacitor or a bank of capacitors. The electronic package 28 comprises electronic components including at least one integrated circuit 32, and discrete, surface mounted components 29 such as capacitors, resistors, switches, etc., that are typically found in ICDs, located on a generally planar substrate 27. The electronic components are fixedly connected to the substrate 27 with interconnect metallization (not shown) within the substrate thereby interconnecting the electronic components together. The circuitry may correspond to any known subcutaneous ICD circuit.

In typical subcutaneous ICD embodiments, a sense amplifier or amplifiers and a pulse generator or generators within a pacing circuitry are connected to the feedthrough in the housing or the housing itself. According to an embodiment of the present invention, a sense amplifier and a pulse generator are coupled to the feedthrough 22 at connection point 24 and to the header 14 fitted on the housing 4. Thus, electrical communication to and from pacing and sensing electrodes, which are included in the electronic package 28, is accomplished using the header fixed on the outer surface of the housing 4 and one or more feedthroughs 22, while retaining hermeticity of the subcutaneous ICD.

Electronic package 28 and power circuit 12 are held within the housing by frame 34. The frame may be made of plastic fitted into the housing to hold the electronic package and the power circuit by way of compression. Alternatively, a flex circuit that interconnects the power circuit, the electronic package and the feedthrough to the housing may be used as a self-supporting frame. In an alternative embodiment, molded plastic cups or clips may be used for arrangement of the power circuit and hybrid electronics components in the subcutaneous ICD.

Insulator 8 is disposed between the housing 4 and the electronic package 28 and the power circuit 12. The insulator 8 may comprise materials such as polycarbonate, polyimide, parylene, and the like. The insulator 8 is applied prior to welding of the housing halves to insulate the housing from the power circuit and the electronic package.

Figure 21:
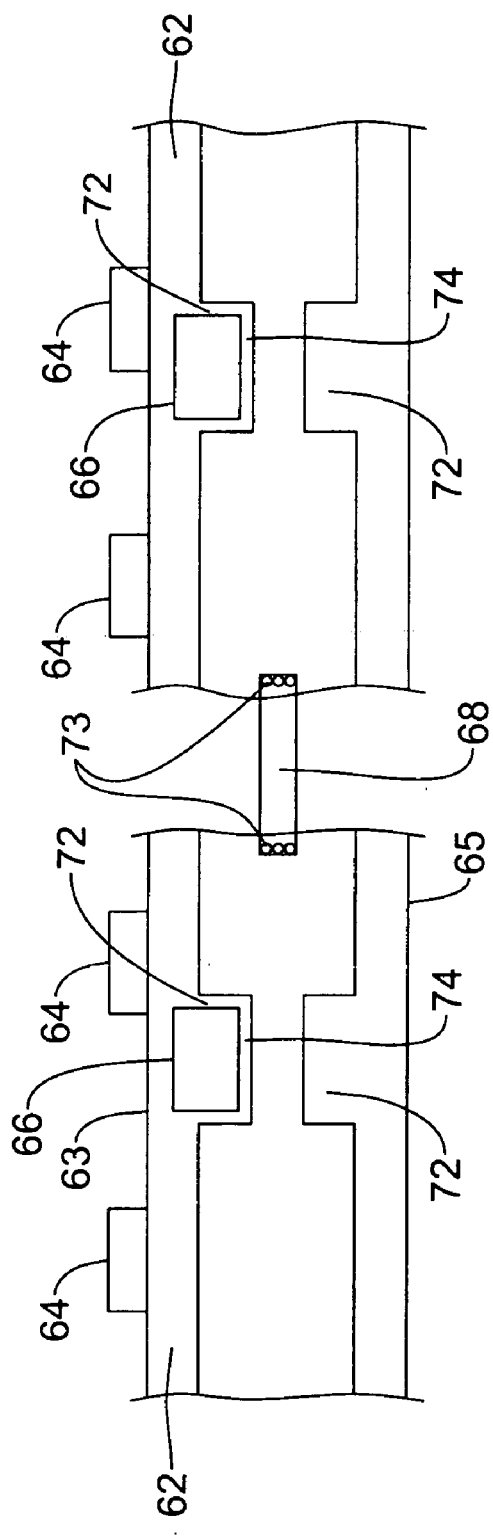
FIG. 21 is a cross sectional view of an electronic package according to an embodiment of the present invention.

Referring now to FIG. 21, a cross sectional view of an electronic package according to the present invention is provided. Electronic package 60 includes at least one integrated circuit (IC) 66 and associated electronic components 64 disposed on a substrate 62. The electronic components are fixedly connected to the substrate with interconnect metallization (not shown) within the substrate thereby interconnecting the electronic components together. The electronic components are discrete components that may be passive such as capacitors, resistors, etc., or active such as diodes and the like. The substrate 62 generally comprises a high-temperature co-fired ceramic, a low-temperature co-fired ceramic, glass epoxy, polyamide, or an equivalent material.

The integrated circuit may include a bare or exposed chip, or may be encapsulated or embedded in a package with electrical contact pads. The IC or electronic components may be positioned within the thickness of the substrate 62 in a cavity 72. Cavity 72 has dimensions greater than corresponding dimensions of ICs or electronic components to be received therein. According to embodiments of the invention, the IC or electronic component is installed near or at the bottom of the cavity 72 using a predetermined thickness of bonding material 74, for example, glue, solder paste, etc., between the IC or electronic component and the bottom of cavity 72. The cavity is filled with an encapsulant to cover the IC or electronic component, which may comprise silicone or epoxy resins, or other semiconductor encapsulants. It is then possible to place additional ICs or electronic components above the cavity. Alternative techniques for mounting electronic components in a cavity will be discussed further with respect to FIG. 22 below.

Figure 22:
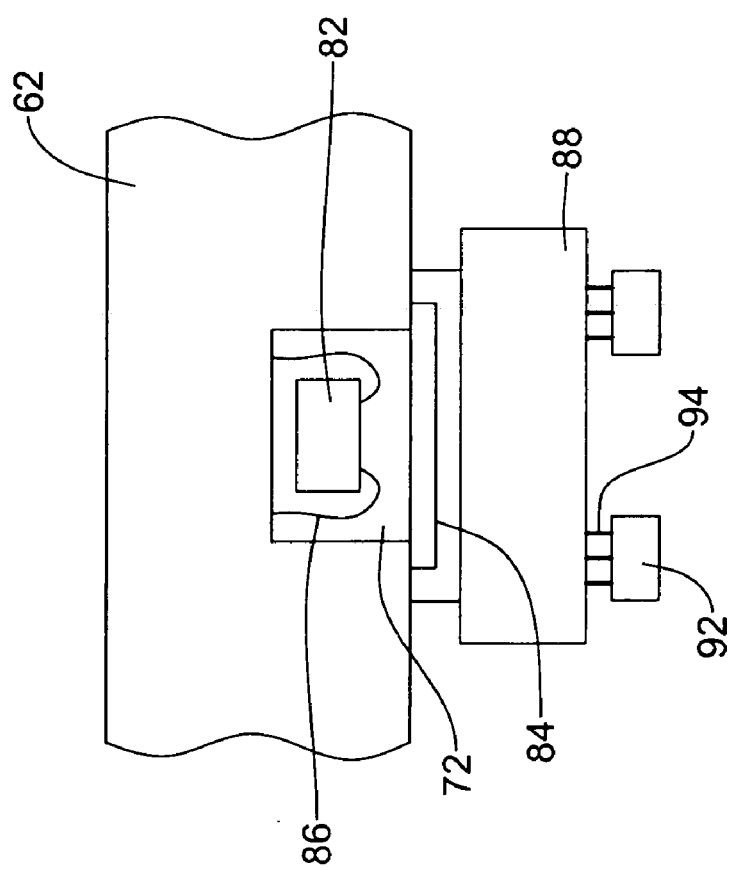
FIG. 22 illustrates a mounting detail of a bare die component in a cavity according to an embodiment of the present invention.

FIG. 22 illustrates a mounting detail of a bare die component in a cavity according to an embodiment of the present invention. A bare die component 82, which may comprise an electronic component, a bare die IC, a bare thin film resistor, etc., is placed in cavity 72 of the substrate 62. The bare die component 82 is typically either glued or mounted with wire bonds 86 from the top of the bare die component to metallization on the substrate 62. In this embodiment, the bare die component 82 is protected with a lid 84, which is typically made of Kovar material, and is placed on top of the cavity 72. The lid 84 is bonded down making a hermetic enclosure for the bare die component 82.

In other embodiments of the invention, instead of a lid on the cavity 72 to protect components, an encapsulation technique may be used. The components may be traditionally bonded, then glob-topped, which is a known encapsulation method using a highly-insulated epoxy or silicon. Other mounting technologies may be used when placing the bare die 82 in the cavity 72, for example, a ball grid array, or a leadless chip carrier. Once the bare die components in a cavity are protected, extra layers of substrate 88 can be applied on top of the cavity 72, thus increasing the density of the substrate. Components 92, which may be surface mounted or ICs can then be located on substrate 88 using a wire bond technique as described above, a glob-top technique, a ball grid array (BGA) technique that uses carriers 94, a leadless chip carrier, or flip-chip techniques.

Referring back to FIG. 21, electronic package 60 may be a double-sided circuit having electronic components on both surfaces 63 and 65 of the substrate 62. Cavities 72 are disposed on one or both surfaces 63 and 65 in which electronic components may be disposed using any of the techniques discussed above such as wire bonding, ball grid array techniques, leadless chip carriers, etc. It should also be noted that embodiments of the invention may comprise a substrate without any cavities.

According to an embodiment, the subcutaneous ICD assembly uses a ribbon or flexible interconnect circuitry 68 to connect the electronic components, the power circuit and the output feedthroughs. The ends of the flex cable 68 are connected at electrical connections 73, for example, by soldering. The power circuit 12 (shown in FIG. 20) has terminals (not shown) that extend up from its top that are connected to the electronic package 28 either by way of the flex cable 68 or individual discrete wires. It should be noted that other interconnecting techniques may be used such as an integrated interconnect circuitry, which combines the functions of a protective cover for the substrate and the flexible interconnect circuitry.

While the present invention has been described above in terms of specific embodiments, it is to be understood that the invention is not limited to the disclosed embodiments. On the contrary, the present invention is intended to cover various modifications and equivalent methods and structures included within the spirit and scope of the appended claims.

What is claimed is:

1. A method for packaging a subcutaneous implantable cardioverter/defibrillator comprising the steps of:
   providing a housing having an inner surface and an outer surface, and a first subcutaneous electrode disposed on the outer surface;
   placing a frame on the inner surface of the housing;
   using the frame to hold a power source, a power storage circuit and an electronic package on a substrate within the housing;
   mounting an electronic component of the electronic package in a cavity of the substrate;
   applying at least one extra layer of substrate on top of the cavity once the electronic components in the cavity are mounted;
   interconnecting the power source, the power storage circuit and the electronic package to the frame;
   fitting a header along a portion of the outer surface of the housing, the header having a connector block embedded therein;
   connecting the electronic package to a feedthrough, which is in turn connected to the connector block;
   providing a septum covered hole in the header adapted to receive a lead, the lead coupled to a second subcutaneous electrode; and
   tightening the lead into the septum covered hole by using a tool;
   wherein a cardioversion-defibrillation energy is delivered between the first and the second subcutaneous electrodes without a transvenous, intracardiac, or epicardial electrode.

2. The method of claim 1 further comprising the step of puncturing the septum covered hole for receiving the lead.

3. The method of claim 1, further comprising the step of forming the housing by attaching a first half to a second half adapted to fit each other.

4. The method of claim 1, further comprising the step of applying an insulator between the inner surface of the housing and the electronic package.

5. The method of claim 3 further comprising the step of welding the first half to the second half to form the housing.

6. The method of claim 5, further comprising applying an insulator between the inner surface of the housing and the electronic package before welding the first half to the second half of the housing.

7. The method of claim 5 further comprising the step of backfilling the housing with a gas to reduce arching inside the housing.

8. The method of claim 7 wherein the gas further comprises approximately 90–95% Nitrogen gas.

9. The method of claim 7 wherein the gas further comprises approximately 5 to 10% Helium.

10. The method of claim 1 further comprising the step of falling dead spaces in the housing with a desiccant.

11. The method of claim 1 further comprising mounting the electronic component using a ball grid array.

12. The method of claim 1 further comprising mounting the electronic component using a leadless chip carrier.

13. The method of claim 1 further comprising mounting the electronic component using a flip chip technology.

14. The method of claim 1 further comprising filling the cavity with an encapsulant to cover the electronic component.

15. The method of claim 1 wherein the electronic component further comprises a bare chip.

16. The method of claim 15, further comprising mounting the bare chip in the cavity by using at least one wire bond.

17. The method of claim 15, further comprising providing a cavity lid to protect the bare chip.

18. The method of claim 1 wherein the electronic component further comprises an encapsulated chip.

19. The method of claim 18, further comprising using glob-top to embed the encapsulated chip in the cavity.

20. The method of claim 1 further comprising the step of placing additional electronic components on top of the extra layers of substrate.

21. The method of claim 20, further comprising the step of using a ball grid array technique to place the additional electronic components on the extra layers of substrate.

22. The method of claim 20, further comprising the step of using a leadless chip carrier to place the additional electronic components on the extra layers of substrate.

23. The method of claim 20, further comprising the step of using flip chip technology to place the additional electronic components on the extra layers of substrate.

24. The method of claim 1 wherein the step of interconnecting further comprises using a flex circuit.

25. The method of claim 1 wherein the step of interconnecting further comprises using discrete wires.

26. A non-transvenous implantable cardioverter/defibrillator comprising:
- a housing having an outer surface, at least a portion of the outer surface being electrically active;
- a frame within the housing for holding electronic components;
- a first subcutaneous electrode and a second subcutaneous electrode, the first and second subcutaneous electrodes electrically coupled to electronic components within the housing, and wherein a cardioversion-defibrillation energy is delivered between the electrically active outer surface of the housing and at least one of the first and second subcutaneous electrodes without a transvenous, intracardiac, or epicardial electrode;
- an electronic package disposed on a substrate electrically coupled to the frame, wherein the electronic package is a double-sided circuit having electronic components on a top surface and a bottom surface of the substrate; and
- a header disposed on the housing comprising at least one feedthrough extending through the housing for providing electrical communication to and from the electronic components within the housing.

27. The non-transvenous implantable cardioverter/defibrillator of claim 26, wherein the frame further comprises a self-supporting flex circuit for holding the electronic components.

28. The non-transvenous implantable cardioverter/defibrillator of claim 26, wherein the flex circuit further comprises solder to hold the electronic components.

29. The non-transvenous implantable cardioverter/defibrillator of claim 26 wherein one of the first or second subcutaneous electrodes is disposed on the lead.

30. The non-transvenous implantable cardioverter/defibrillator of claim 29, wherein the first subcutaneous electrode is disposed on the housing and the second subcutaneous electrode is disposed on the lead.

31. A subcutaneous implantable cardioverter/defibrillator comprising:
- a housing having an inner surface and an outer surface, at least a portion of the outer surface being electrically active;
- a frame disposed on the inner surface of the housing;
- a power circuit electrically coupled to the frame;
- an electronic package disposed on a substrate electrically coupled to the frame and to the power circuit, wherein the substrate comprises a cavity sized to receive an electronic component of the electronic package, and at least one extra layer of substrate applied on top of the cavity;
- a first subcutaneous electrode and a second subcutaneous electrode, the first and second subcutaneous electrodes electrically coupled to the electronic package, and wherein a cardioversion-defibrillation energy is delivered between the electrically active outer surface of the housing and at least one of the first and second subcutaneous electrodes without a transvenous, intracardiac, or epicardial electrode, and
- a header fixed on a portion of the outer surface of the housing wherein the header comprises at least one feedthrough extending through the housing to allow electrical communication to and from the electronic package within the housing.

32. The subcutaneous implantable cardioverter/defibrillator of claim 31 wherein the housing further comprises a first half and a second half adapted to fit each other.

33. The subcutaneous implantable cardioverter/defibrillator of claim 32, wherein the first half and the second half of the housing are welded together.

34. The subcutaneous implantable cardioverter/defibrillator of claim 33, wherein the housing is backfilled with gas to prevent potential arching inside the housing.

35. The subcutaneous implantable cardioverter/defibrillator of claim 33, wherein the gas further comprises approximately 90–95% Nitrogen gas.

36. The subcutaneous implantable cardioverter/defibrillator of claim 33, wherein the gas further comprises approximately 5 to 10% Helium.

37. The subcutaneous implantable cardioverter/defibrillator of claim 33, wherein the housing further comprises dead spaces filled with a desiccant.

38. The subcutaneous implantable cardioverter/defibrillator of claim 31 wherein the housing further comprises a material selected from the group consisting essentially of ceramics, titanium, stainless steel, and Nickel alloys.

39. The subcutaneous implantable cardioverter/defibrillator of claim 31 wherein the frame further comprises a plastic material.

40. The subcutaneous implantable cardioverter/defibrillator of claim 31 wherein the frame further comprises a self-supporting flex circuit.

41. The subcutaneous implantable cardioverter/defibrillator of claim 31 wherein the header further comprises materials selected from the group consisting essentially of polyurethane, silicone and epoxy.

42. The subcutaneous implantable cardioverter/defibrillator of claim 31 further comprising a connector block embedded in the header adapted to connect a lead and making an attachment to the at least one feedthrough.

43. The subcutaneous implantable cardioverter/defibrillator of claim 1 wherein the at least one feedthrough further comprises a hermetic wire.

44. The subcutaneous implantable cardioverter/defibrillator of claim 31 wherein the at least one feedthrough further comprises at least one of plastic insulation, ceramics and glass.

45. The subcutaneous implantable cardioverter/defibrillator of claim 31 wherein the header further comprises a pre-slit septum covered hole adapted to be punctured with a tool, the septum covered hole positioned to receive a lead.

46. The subcutaneous implantable cardioverter/defibrillator of claim 31 wherein the electronic package further comprises at least one integrated circuit.

47. The subcutaneous implantable cardioverter/defibrillator of claim 31 wherein the electronic package further comprises surface mounted components.

48. The subcutaneous implantable cardioverter/defibrillator of claim 47 wherein the surface mounted components further comprise capacitors.

49. The subcutaneous implantable cardioverter/defibrillator of claim 47 wherein die surface mounted components further comprise resistors.

50. The subcutaneous implantable cardioverter/defibrillator of claim 31 wherein the power circuit further comprises at least one battery.

51. The subcutaneous implantable cardioverter/defibrillator of claim 31 wherein the power circuit further comprises at least one high-voltage capacitor.

52. The subcutaneous implantable cardioverter/defibrillator of claim 31 further comprising an insulator positioned between the inner surface of the housing and the electronic package and the power circuit.

53. The subcutaneous implantable cardioverter/defibrillator of claim 52 wherein the insulator further comprises a material selected from the group consisting essentially of polycarbonate, polyimide, and parylene.

54. The subcutaneous implantable cardioverter/defibrillator of claim 31 wherein the substrate further comprises a material selected from the group consisting essentially of a high-temperature co-fired ceramic, a low-temperature co-fired ceramic, an epoxy and a polyimide.

55. The subcutaneous implantable cardioverter/defibrillator of claim 31 wherein the electronic package further comprises a bare chip.

56. The subcutaneous implantable cardioverter/defibrillator of claim 31 wherein the electronic package further comprises an encapsulated chip.

57. The subcutaneous implantable cardioverter/defibrillator of claim 31 wherein the electronic component is mounted near a bottom of the cavity.

58. The subcutaneous implantable cardioverter/defibrillator of claim 31 wherein the electronic component further comprises a bare chip.

59. The subcutaneous implantable cardioverter/defibrillator of claim 58 wherein the bare chip is mounted with wire bonds from top of the bare chip to metallization on the substrate.

60. The subcutaneous implantable cardioverter/defibrillator of claim 58 wherein the bare chip is glob-topped.

61. The subcutaneous implantable cardioverter/defibrillator of claim 31 wherein the electronic component further comprises an encapsulated chip with glob-top.

62. The subcutaneous implantable cardioverter/defibrillator of claim 31 wherein the electronic component further comprises a ball grid array.

63. The subcutaneous implantable cardioverter/defibrillator of claim 31 wherein the electronic component further comprises a leadless chip carrier.

64. The subcutaneous implantable cardioverter/defibrillator of claim 31, wherein the electronic component further comprises flip chip technology.

65. The subcutaneous implantable cardioverter/defibrillator of claim 31 wherein the cavity is filled with an encapsulant to cover the electronic component.

66. The subcutaneous implantable cardioverter/defibrillator of claim 31 further comprising a lid placed on top of the cavity.

67. The subcutaneous implantable cardioverter/defibrillator of claim 66 wherein the lid further comprises kovar material.

68. The subcutaneous implantable cardioverter/defibrillator of claim 31 further comprising electronic components mounted on the at least one extra layer of substrate.

69. The subcutaneous implantable cardioverter/defibrillator of claim 68 wherein the electronic components are mounted on the at least one extra layer of substrate by using a ball grid array.

70. The subcutaneous implantable cardioverter/defibrillator of claim 68 wherein the electronic components are mounted on the at least one extra layer of substrate by using a wire bond.

71. The subcutaneous implantable cardioverter/defibrillator of claim 68 wherein the electronic components are mounted on the at least one extra layer of substrate by using a wire bond with glob top.

72. The subcutaneous implantable cardioverter/defibrillator of claim 68 wherein the electronic components are mounted on the at least one extra layer of substrate by using a leadless chip carrier.

73. The subcutaneous implantable cardioverter/defibrillator of claim 68 wherein the electronic components are mounted on the at least one extra layer of substrate by using flip chip technology.

74. The subcutaneous implantable cardioverter/defibrillator of claim 68 wherein the substrate has a lower surface and an upper surface.

75. The subcutaneous implantable cardioverter/defibrillator of claim 68 wherein the electronic package further comprises electronic components disposed on at least one of the lower surface and the upper surface of the substrate.

76. The subcutaneous implantable cardioverter/defibrillator of claim 74 wherein the lower surface and the upper surface of the substrate further comprise at least one cavity.

77. The subcutaneous implantable cardioverter/defibrillator of claim 31 further comprising a flexible circuit to interconnect the electronic package, the power circuit, and the at least one feedthrough.

78. The subcutaneous implantable cardioverter/defibrillator of claim 31 wherein the power circuit is interconnected to the electronic package by discrete wires.

* * * * *

UNITED STATES PATENT AND TRADEMARK OFFICE
CERTIFICATE OF CORRECTION

PATENT NO. : 7,194,309 B2
APPLICATION NO. : 10/011607
DATED : March 20, 2007
INVENTOR(S) : Alan H. Ostroff et al.

Page 1 of 1

It is certified that error appears in the above-identified patent and that said Letters Patent is hereby corrected as shown below:

Column 9
Line 30, delete "*inframmary*", and insert therefor -- *inframammary* --.
Line 35, after "left" and before "crease", insert -- inframammary --.
Line 47, delete "pat" and insert therefor -- path --.
Line 56, delete "shalt", and insert therefor -- shaft --.

Column 10
Line 4, delete "10)", and insert therefor -- ICD --.

Column 14
Line 1, delete "tat", and insert therefor -- that --.

Column 18
Line 32, delete "falling", and insert therefor -- filling --.

Column 20
Line 55, delete "die", and insert therefor -- the --.

Column 22
Line 28, delete "claim 68", and insert therefor -- claim 31 --.
Line 31, delete "claim 68", and insert therefor -- claim 74 --.

Signed and Sealed this

Eighth Day of May, 2007

JON W. DUDAS
*Director of the United States Patent and Trademark Office*